US007449192B2

(12) United States Patent
Schmidt

(10) Patent No.: US 7,449,192 B2
(45) Date of Patent: *Nov. 11, 2008

(54) USE OF NEUROTOXIN THERAPY FOR TREATMENT OF UROLOGIC AND RELATED DISORDERS RELATED TO NEUROGENIC BLADDER DYSFUNCTION

(75) Inventor: Richard A. Schmidt, Arvada, CO (US)

(73) Assignee: The Regents of the University of Colorado, Denver, CO (US)

( * ) Notice: Subject to any disclaimer, the term of this patent is extended or adjusted under 35 U.S.C. 154(b) by 283 days.

This patent is subject to a terminal disclaimer.

(21) Appl. No.: 10/778,924

(22) Filed: Feb. 13, 2004
(Under 37 CFR 1.47)

(65) Prior Publication Data
US 2005/0048084 A1 Mar. 3, 2005

Related U.S. Application Data

(63) Continuation-in-part of application No. 10/685,995, filed on Oct. 14, 2003, which is a continuation of application No. 09/978,982, filed on Oct. 15, 2001, now Pat. No. 6,667,041, which is a continuation of application No. 09/463,040, filed as application No. PCT/US98/14625 on Jul. 15, 1998, now Pat. No. 6,365,164.

(60) Provisional application No. 60/052,580, filed on Jul. 15, 1997.

(51) Int. Cl.
*A61K 39/08* (2006.01)
*A61K 39/02* (2006.01)
*A61K 49/00* (2006.01)

(52) U.S. Cl. .............. 424/247.1; 424/239.1; 424/236.1; 424/234.1; 424/9.1

(58) Field of Classification Search ................ 424/239.1
See application file for complete search history.

(56) References Cited

U.S. PATENT DOCUMENTS

| 4,932,936 | A | 6/1990 | Dykstra et al. ............... 604/511 |
|---|---|---|---|
| 5,183,462 | A | 2/1993 | Borodic |
| 5,437,291 | A | 8/1995 | Pasricha et al. ............. 128/898 |
| 5,674,205 | A * | 10/1997 | Pasricha et al. ............. 604/232 |
| 5,837,265 | A | 11/1998 | Montal et al. ............. 424/239.1 |
| 5,919,665 | A | 7/1999 | Williams .................... 435/71.1 |
| 5,939,070 | A | 8/1999 | Johnson et al. .......... 424/194.1 |
| 5,989,545 | A | 11/1999 | Foster et al. ............. 424/183.1 |
| 6,306,423 | B1 | 10/2001 | Donovan et al. ............ 424/423 |
| 6,312,708 | B1 | 11/2001 | Donovan .................... 424/423 |
| 6,365,164 | B1 | 4/2002 | Schmidt ................... 424/239.1 |
| 6,383,509 | B1 | 5/2002 | Donovan et al. ............ 424/423 |
| 6,506,399 | B2 | 1/2003 | Donovan .................... 424/423 |
| 6,585,993 | B2 | 7/2003 | Donovan et al. ............ 424/423 |
| 6,667,041 | B2 | 12/2003 | Schmidt |
| 7,001,602 | B2 | 2/2006 | Schmidt |
| 7,153,514 | B2 | 12/2006 | Schmidt |
| 2004/0180065 | A1 | 9/2004 | Schmidt |
| 2005/0048084 | A1 | 3/2005 | Schmidt |
| 2005/0049175 | A1 | 3/2005 | Schmidt |
| 2005/0112147 | A1 | 5/2005 | Schmidt |
| 2005/0159337 | A1 | 7/2005 | Schmidt |

FOREIGN PATENT DOCUMENTS

| JP | 6-183975 | 7/1994 |
|---|---|---|
| JP | 8-511537 | 12/1996 |
| WO | WO 95/05842 | 3/1995 |
| WO | WO 95/17904 | 7/1995 |
| WO | WO 99/03483 | 1/1999 |

OTHER PUBLICATIONS

Jankovich et al. "Botulinum toxin in movement disorders". Current Opinion in Neurology. Aug. 1994, vol. 7, No. 4, pp. 358-366.*
Beleggia et al., Arch. It. Urol., LXIX, (S.1): 61-63, 1997 (English Abstract).
Chancellor et al., J Urol Apr. 2003;169 (Supp 4):351.
DasGupta et al., Urogynaecology 2003, 13:293-299.
Fowler et al., British J of Urol., Oct. 22, 1991, 387-389.
Kuo, Hann-Chorng, J Urol Nov. 2003, 170:1908-1912.
Leippold et al., Eur Urol 44 (2003) 165-174.
Nanninga, John B., Oxins (1993) p. 589-590.
Smith et al., Int Urogynecol J (2002) 13:55-56.
Bruschini et al., "Neurologic Control of Prostatic Secretion in the Dog"; *Invest. Urol.*, 15(4):288-290 (Jan. 1978).
Downie et al., "Evidence for a Spinal Site of Action of Clonidine on Somatic and Viscerosomatic Reflex Activity Evoked on the Pudendal Nerve in Cats"; *J. Pharmacol. Exp. Ther.*, 246(1):352-358 (May 1988).
* Dykstra et al.; "Effects of Botulinum a Toxin on Detrusor-Sphincter Dyssynergia in Spinal Cord Injury Patients"; *J. Urology*; 139:919-922; (May 1988).
Dykstra et al., "Treatment of Detrusor-Sphincter Dyssynergia with Botulinum A Toxin: A Double-Blind Study"; *Arch. Phys. Med. Rehabil.*, 71:24-26 (Jan. 1990).
Hàkanson et al., "Multiple Tachykinin Pools in Sensory Nerve Fibres in the Rabbit Iris"; *Neuroscience*, 21(3):943-950 (1987).
Higgins et al., "Studies on the Structure and Intrinsic Innervation of the Normal Human Prostate"; *Prostate Suppl.*, 2:5-16 (1989).
Ishizuka et al., "Urodynamic Effects of Intravesical Resiniferatoxin and Capsaicin in Conscious Rats With and Without Outflow Obstruction"; *J. Urology*, 154:611-616 (Aug. 1995).

(Continued)

*Primary Examiner*—Vera Afremova
(74) *Attorney, Agent, or Firm*—Sheridan Ross P.C.

(57) ABSTRACT

The present invention related to methods for treating neurological-urological conditions, including neurogenic bladder dysfunction. This is accomplished by administration of a botulinum toxin into the lower urinary tract of a patient with a neurogenic bladder dysfunction, including the bladder or urinary sphincter and the bladder wall.

8 Claims, No Drawings

OTHER PUBLICATIONS

Joo et al., "Initial North American Experience with Botulinum Toxin Type A for Treatmetn of Anismus"; *Dis. Colon. Rectum*, 39(10):1107-1111 (Oct. 1996).
Lepor "Role of Long-Acting Selective Alpha-1 Blockers in the Treatment of Benign Prostatic Hyperplasia"; *Urol. Clin. North Am.*, 17(3):651-658 (Aug. 1990).
Maggl et al., "Cystometric Evidence That Capsacin-Sensitive Nerves Modulate the Afferent Branch of Micturition Reflex in Humans"; *J. Urol.*, 142:150-154 (Jul. 1989).
* -Maria et al.; "Relief by Botulinum Toxin of Voiding Dysfunction Due to Prostatitis"; *The Lancet*; 352:625; (Aug. 1998).
Mocchetti, "Pharmacology of Neuronal Gene Expression"; *Pharmacol. Res.*, 21(Suppl. 2):85-95 (1989).
Schurch et al., *J. Urol.*, 155:1023-1029 (1996).
* Schurch et al.; "Effects of Botulinum A Toxin on the Periurethral Striated Spincter of the Neurogenic Bladder: Preliminary Study"; *J. Urology*; 96(7):375-80; (1990).
* Striker; "Special Communication: Kuh Notes"; *J. Urology*; 136:919; (Oct. 1986).
Tim et al., *Botulinum Toxin Therapy*, 9(6):327-332 (1992).
Amarenco, Pour la pratique, Lae Revue du Praticien (Paris), 1995, 343-345, 45, France and abstract in English.
Araki et al. Detrusor-Sphincter Dyssynergia with Special Reference to its Diagnosis and Treatment, J. Saitama Med. School, 1992, 23-27, vol. 19, Department of Urology, Saitama Medical School, Moroyama, Iruma-gun, Sitama, Japan.
Bulau, Therapeutische Perspektiven mit Botulinumtoxin Type A., Neurologie und rehabilitation, 1997, 55-56, Germany.
Doggweiler et al., Botox-Induced Prostatic Involution, The Prostate, 1998, 44-50, vol. 37, University of Colorado Health Science Center, Denver, CO, USA.
Dykstra et al., Effects of Botulinum a Toxin on Detrusor-Sphincter Dyssynergia in Spinal Cord Injury Patients, J Urol, May 1998, 919-922, vol. 139, Departments of Physical Medicine and Rehabilitation and Urologic Surgery, University of Minnesota Hospital and Clinic, Minneapolis Minnesota, USA.
Fowler et al., Mytonic-Like EMG Activity of the Urethral Sphincter in Women with Urinary Retention and the Use of Botulinum Toxin to Treat this Disorder, Neurophysiologie Clinique, 1990, 19s, vol. 20, Department of Uro-Neurology, National Hospital for Nervous Diseases, Queen Square and Urology Departments, The London Hospital and the Middlesex Hospital United Kingdom.
Fowler et al., Botulinum Toxin in the Treatment of Chronic Urinary Retention in Women, British Journal of Urology, 1992, 387-389, vol. 70, British Journal of Urology, United Kingdom.
Maria et al., Relief by botulinum toxin of voiding dysfunction due to prostatitis, LANCET (North American Edition), 1998, 625, vol. 352, Departments of Surgery, Urology and Neurology, Catholic University of Rome, Rome, USA.
Harrison, Principles of Internal Medicine, 1987, 196-197, 11th Edition, McGraw-Hill Book Company, New York, New York, USA.
Jankovic, Botulinum toxin in movement disorders, Current Opinion in Neurology, 1994, 358-366, vol. 7, Baylor College of Medicine, Houston, Texas, USA.
Jankovic, Therapeutic uses of Botulinum, The New England Journal of Medicine, 1991, 1186-1194, vol. 324 No. 17, Department of Neurology, Baylor College of Medicine, Houston, Texas, USA.
Karp, et al., Therapeutic Effects of Botulinum Toxins, Handbook of Natural Toxins; Bacterial Toxins and Virulence Factors in Disease, 1995, 1-22, National Institute of Neurological Disorders and Stroke, National Institutes of Health, Bethesda, Maryland, USA.
Punch, Gynaecological, and non-gynaecological, chronic pelvic pain, The Lancet, Feb. 21, 1998, 607, vol. 351, Department of OB/BYN, University of Michigan Medical Center, Women's Hospital, Ann Arbor, Michigan, USA.
Steinhardt et al., Botulinum Toxin Novel Treatment for Dramatic Urethral Dilation Associated with Dysfunctional Voiding, The Journal of Urology, 1997, 190-191, vol. 158, American Urological Association, Inc., St. Louis, Missouri, USA.
Zwergel, et al. Bladder Dysfunction in Disseminated Encephalomyelitis-Drug Therapy and Interventional Methods, Fortschritte Der Neurologie Psychiatrie, 1995, 495-503, vol. 63, Neurologische Klinik der Universitat des Saarlandes, Homburg/Saar, Germany.
Grise, Phillippe, Affidavit, Sep. 26, 2006.
Grosse, Joachim, Affidavit, Sep. 25, 2006.
Carl, Stefan, Affidavit, Sep. 26, 2006.
E. Shapiro et al., "Quantifying the Smooth Muscle Content of the Prostate . . . ", The Journal of Urology 147 (1992), pp. 1167 to 1170.
G.E. Borodic and L.B. Pearce, "New Concepts in Botulinum Toxin Therapy", Drug Safety 11 (1994), pp. 145-152.
Internet presentation on prostate disorders and the anatomy of the prostate/bladder: http://www.familydoctor.co.uk/htdocs/PROSTATE/PROSTATE_specimen.html (printed on Dec. 11, 2006).
Internet presentation on prostatitis: http://www.urology-health.org/adult/index.cfm?cat=07&topic=15 (printed on Dec. 11, 2006).
Entry for "benigne Prostatahyperblasie" in Pschyrembel, klinisches Worterbuch (257.Auflage, 1994).
Martinez-Pinero et al., "Pelvic Plexus Denervation in Rats Causes Morphologic and Functional Changes of the Prostate", The Journal of Urology 150 (1993), pp. 215-218.
Amarenco, "Evaluation et Traitement des Dysfonctionnements Vesico-Sphincteriens Neurogenes" Annales d'Urologie 27(1993) pp. 313-320.
Medical Pharmacology at a Glance, Blackwell Scientific Publications, 1987- pp. 18-19.
1996 MIMS Annual, Australian Edition. The entry for Botulinum Toxin is located at 5-372.
U.S. Appl. No. 11/925,938, filed Oct. 27, 2007, Schmidt.
U.S. Appl. No. 11/925,942, filed Oct. 27, 2007, Schmidt.
U.S. Appl. No. 11/925,945, filed Oct. 27, 2007, Schmidt.
"AFUD Prostate Cancer Treatment: Treatment"; American Foundation for Urologic Disease; (at least as early as Aug. 5, 2003).
"Continence Management"; The Prostate Cancer Charity; (at least as early as Aug. 8, 2003); 6 pp.
"Inconsistence and the Prostate"; Phoenix5; (at least as early as Aug. 5, 2003); 11 pp.
"Prostate Cancer (PDQ®): Treatment"; National Cancer Institute; (Jul. 17, 2003); 11 pp.
"Prostate Cancer: Prostate Cancer Transrectal Biopsies"; (at least as early as Aug. 20, 2003); 9 pp.
"Prostate Cancer: Tumor Grading"; UPMC Cancer Centers; (2003); 2 pp.
"Prostate Cancer: What are the Treatment Options?"; NSW Health; (Jan. 4, 2002); 2 pp.
"Prostate Gland and Urinary Problems"; Better Health Channel; (Oct. 10, 2001); 10 pp.
"Questions and Answers About the Prostate-Specific Antigen (PSA) Test"; National Cancer Institute; (Jan. 11, 2001); 5 pp.
"The Side Effects of Treatment"; Varian Medical System; (1999-2003); 2 pp.
"Treating Prostate Disease"; The Cleveland Clinic; (Jan. 28, 1999); 3 pp.
"Understanding Gleason Grading"; Phoenix5; (May 14, 1997); 8 pp.
Bardsley; "The Neurogenic Bladder"; Art & Science Continence; (Jan. 7, 2000); pp. 39-41.
BladderInfo.com: Bladder Control Problems 2004 Pfizer, Inc. www.overactivebladderhelp.com/conditions/problems_bladder.htm, pp. 1-3.
BladderZone.com: Bladder Problems Explained, Pfizer, Ltd., www.bladderzone.com/info/bladder_expl.htm, Copyright 2003, pp. 1-2.
Boyd, et al., Lancet 1996 348:481-82.
Burnstein et al.; "Prostatitis: A Difficult Diagnosis"; Dekalb Clinic Urology; (at least as early as Aug. 20, 2003); 3 pp.
Crawford; "Prostate Cancer"; Best Doctors; (Jun. 7, 2000); 6 pp.
Epstein;"Gleason Score 2-4 Adenocarcinoma of the Prostate on Needle Biopsy"; American Journal of Surgical Pathology; (2000) vol. 24(4); pp. 477-78.
Han et al., "Botulinum toxin A injection for the treatment of detrusor external sphincter dyssynergia", (translated abstract), Apr. 2006, pp. 1-3.
Khastgir and Shah, Urology News 2001 5:6-8.

Marieb; "Chapter 13: Peripheral Nervous System and Reflex Activity"; Human Anatomy and Physiology. 5th Ed.; (at least as early as Aug. 8, 2003) 5 pp.

Peak; "Understanding Continence"; The Interdisciplinary Journal of Rehabilitation; (Mar. 2002); 9 pp.

Strum; "Is There a Correct Way to Treat Prostate Cancer"; Prostate Cancer Research Institute; 28 pp. (at least as early as Sep. 12, 2000).

Strum; "Preductive and Prognostic Information in the Counseling of Patients Recently Diagnosed with Prostate Cancer"; The Prostate Cancer Research Institute; (at least as early as Sep. 12, 2000); 21 pp.

Treatment for Localized Disease: Observation and Monitoring of PSA; Prostate Cancer Research Institute; (at least as early as Aug. 11, 2003); 1 p.

"Symptoms & Treatments"; Multiple Sclerosis International Federation; pp. 1-6; (as early as 2003).

"Western Multiple Sclerosis Center's Glossary"; UW Medicine; (at least before Sep. 30, 2003); pp. 1-15.

MS-Network.com Glossary, Section C; Benecke NI; 2000, pp. 1-4.

* cited by examiner

USE OF NEUROTOXIN THERAPY FOR TREATMENT OF UROLOGIC AND RELATED DISORDERS RELATED TO NEUROGENIC BLADDER DYSFUNCTION

CROSS REFERENCE TO RELATED APPLICATIONS

This application is a continuation-in-part of U.S. patent application Ser. No. 10/685,995, filed Oct. 14, 2003, which is a continuation of U.S. patent application Ser. No. 09/978,982, filed Oct. 15, 2001, now U.S. Pat. No. 6,667,041, which is a continuation of U.S. patent application Ser. No. 09/463,040, filed Jan. 17, 2000, now U.S. Pat. No. 6,365,164, which is a 371 of PCT Application No. PCT/US98/14625, filed Jul. 15, 1998, which claims priority under 35 U.S.C. § 119(e) to U.S. Provisional Application Ser. No. 60/052,580, filed Jul. 15, 1997. The entire disclosure of each of the above-referenced applications is incorporated herein by reference.

FIELD OF THE INVENTION

The present invention provides methods for treating neuronally-mediated urologic and related disorders, for example, neurogenic bladder dysfunction. This is accomplished by administering a composition that includes at least one neurotoxic compound such as botulinum toxin into the lower urinary tract, including the bladder wall and the urinary sphincter or bladder neck, or by conventional therapies.

BACKGROUND OF THE INVENTION

Many medical conditions in urology are rooted in a spastic dysfunction of the sacral reflex arcs. Examples of such conditions include pelvic pain (e.g., interstitial cystitis, endometriosis, prostatodynia, urethral instability syndromes), pelvic myofascial elements (e.g., levator sphincter, dysmenorrhea, anal fistula, hemorrhoid), urinary incontinence (e.g., unstable bladder, unstable sphincter), prostate disorders (e.g., BPH, prostatitis, prostate cancer), recurrent infection (secondary to spastic sphincter, hypertrophied bladder neck) and neurogenic bladder dysfunction (e.g., Parkinson's Disease, spinal cord injury, stroke, multiple sclerosis, spasm reflex).

Neurogenic bladder dysfunction is a dysfunction that results from interference with the normal nerve pathways associated with urination. Normal bladder function is dependent on the nerves that sense the fullness of the bladder and on those that trigger the muscle movements that either empty it or retain urine. Normally, the reflex to urinate is triggered when the bladder fills to 300-500 ml. The bladder is then emptied when the contraction of the bladder wall forces urine out through the urethra. The bladder, internal sphincters, and external sphincters may all be affected by nerve disorders that create abnormalities in bladder function. The damage can cause the bladder to be underactive, in which it is unable to contract and unable to empty completely, or it can be overactive, in which it contracts too quickly or frequently.

One type of neurogenic bladder dysfunction is overactive (spastic or hyper-reflexive) bladder. An overactive neurogenic bladder is characterized by uncontrolled, frequent expulsion of urine from the bladder. There may be reduced bladder capacity and incomplete emptying of urine. Spastic bladder may be caused by an inability of the detrusor muscle of the bladder to inhibit emptying contractions until a reasonable amount of urine has accumulated. Often, a strong urge to void is experienced when only a small amount of urine is in the bladder. The patient may report symptoms of urgency, frequency, nocturia, and incontinence. Another type of neurogenic bladder dysfunction is characterized by difficulty in relaxing the urinary sphincter muscle. The sphincter may be spastic. This causes difficulty in emptying the bladder, which can lead to urinary retention and urinary tract infections. In another type of neurogenic bladder dysfunction, both the detrusor muscle and the urinary sphincter simultanously contract resulting in urinary retention. A dysfunction associated with simultaneous contraction of both the detrusor and the urinary sphincter is called detrusor-external sphincter dyssynergia (DESD).

There are numerous causes for neurogenic bladder dysfunction. An overactive bladder/sphincter may be caused by interruptions in the nerve pathways to the bladder occurring above the sacrum. This nerve damage results in a loss of sensation and motor control and is often seen in stroke, Parkinson's disease, spina bifida, diabetes, pelvic surgery, or invertebral disc herniation, and most forms of spinal cord injuries. Sometimes no cause is found, and such idiopathic cases may be due to anxiety or aging.

Inability to control urination, also known as urinary incontinence, is perhaps the most common symptom associated with the neurogenic bladder. This may be caused by abnormalities in bladder capacity or malfunction of control mechanisms such as the bladder neck and/or external urethral sphincter muscle that are important for the bladder's storage function. However, not all neurogenic bladder dysfunctions are characterized by urinary incontinence.

Symptoms including a dribbling urinary stream, straining during urination or inability to urinate may also be associated with neurogenic bladder. Urinary retention may result either from loss of bladder muscle contracting performance or loss of appropriate coordination between the bladder muscle and the external urethral sphincter muscle.

Irritating symptoms, such as urinary frequency and urgency, may be evidence of bladder hyperactivity. Other irritating symptoms may include painful urination (dysuria), which may be a result of a urinary tract infection (UTI) caused by urine being held too long in the bladder. UTI with fever is a sign of potential severe kidney infection (pyelonephritis) and is a more worrisome situation as it may result in permanent damage of the kidney(s).

Stones may also form in the urinary tract of individuals with a neurogenic bladder dysfunction caused by the stoppage of urine flow and/or infection.

Abnormal backup of urine from the bladder to the kidney(s), also known as vesicoureteral reflux (VUR), may develop as a means of releasing high pressure within the bladder. A UTI is of particular concern as VUR may place the patient at significant risk for a severe kidney infection by transporting infected bladder urine directly to the kidney(s).

In the past, physicians have tried a number of treatments for neurogenic bladder dysfunction. One treatment option is to use drugs to relax the bladder, such as anticholinergics such as propantheline and oxybutynin. However, these drugs do not act specifically towards the bladder and tend to reduce muscle tone throughout the body, an undesirable side effect. Intermittent catheterization is another treatment that can be used to empty the bladder; however, it often requires a skilled caregiver to place the catheter and is inconvenient to the patient. An indwelling catheter is another option; however, such catheters have several risks including infections and bladder stones. Another treatment option is to simply have the patient wear diapers or other protective type devices to prevent urine leakage and overflow from wetting clothing and/or bedding.

Another embodiment of the present invention relates to another type of urological-neurological dysfunction associated with the prostate. The prostate is a partially glandular and partially fibromuscular organ of the male reproductive system. During aging, the prostate tends to enlarge (hypertrophy). This prostatic enlargement can lead to urethral obstruction and voiding dysfunction.

Prostatic enlargement is a common occurrence in older men. Lytton et al. (Lytton, B., Emery, J. M and Harvard, B. M. [1973] 99: 639-645) estimated that a 45 year old male had a 10% risk of prostate surgery by age 70. The U.S. Census Report estimates that there are 30 million people today over age 65. This segment of the population is projected to rise to 50 million over the next 30 years. Therefore, the number of men with prostatic enlargement also will increase. According to draft reports of the National Kidney and Urologic Disease Advisory Board, 425,000 prostatectomies were performed in the United States in 1989. Based on population growth estimates, the number of prostatectomies performed annually will rise to 800,000/year by the year 2020.

The urethra passes through the prostate (prostatic urethra) as it courses to the external urethral orifice. The prostate has five distinct lobes that are apparent at 12 weeks in the human fetus (Lowsley, O. S. Am. J. Anat. [1912] 13: 299-349.). Although the lobular branching found in the fetus is not visible in the prepubescent prostate, the lateral middle anterior and posterior lobes are used to describe the enlarged prostate.

A more recent viewpoint is that the prostate also is comprised of several morphologically distinct zones (McNeaL, J. Urol. Clin. North Am. [1990] 17(3): 477-486). The majority of the glandular volume is composed of the peripheral zone (~70-75%). The remainder of glandular volume is divided into the central zone (~20-25%), the transition zone (~5-10%) and the periurethral glandular zone (~1%).

McNeal (1990) reported that BPH develops in the transition zone and the periurethral glandular zone. BPH nodules develop either within or immediately adjacent to the prepostatic sphincteric zone. The transition zone is a small region close to the urethra intimately related to the proximal urethral sphincter. The stroma of the transition zone is dense and compact, and is unusually susceptible to neurologically-induced disturbances of growth control. Its glands penetrate the sphincter, while sphincter muscle fibers penetrate the transition stroma. The periurethral glandular zone has a similar urogenic sinus origin as the transition zone.

BPH may be associated with increased amounts of stroma relative to epithelium (Bartsch, G., Muller, H. R., Oberholzer, M, Rohr, H., P., J. Urol. [1979] 122: 487-491). A significant portion of the stroma is smooth muscle (McNeal, 1990) which is under sympathetic nervous control. The contractile properties of this smooth muscle could account for the dynamic component of obstruction in BPH (Bruschini, H. et at. [1978] Invest. Urol. 15(4): 288-90; Lepor, H [1990] Urol. Clin. North Am. 17(3): 651-658).

In addition to sympathetic control of prostatic stroma, the prostate is highly innervated. The prostate nerve fibers enter the prostate from the posterior lateral aspect, with a concentration of ganglia near the junction between the prostate and the seminal vesicles (Maggi, C. A, ed. [1993] Nervous control of the Urogenital System, Harwood Academic Publishers; Higgins, J. R. A. and Gosling, J. A. [1989] Prostate Suppl. 2: 5-16).

Acetylcholine (ACH), neuropeptide Y (NPY), vasoactive intestinal peptide (VIP) and noradrenaline fibers have been described in this gland. A rich plexus of ACH-positive nerve cell bodies is associated with secretory acini in all parts of the gland. Some of the ACH fibers also contain NPY neurons. VIP-containing neurons have been found associated with ACH-containing nerve cell bodies. Occasional neurons have been found between the ACH-staining nerve fibers, suggesting that both NPY and noradrenergic neurons supply smooth muscle (Higgins, J. R. A and Gosling, J. A [1989] Prostate Suppl. 2: 5-16).

Autonomic nerves are distributed evenly between the central and peripheral zones of the prostate (Higgins, J. R. A. and Gosling, J. A [1989] Prostate Suppl. 2: 5-16). Peripheral neuronal control is similar. In addition, there is no difference in the type of nerve fibers, found associated with either epithelial or stromal elements of the gland.

The anatomical studies of nerve fiber types in the prostate, coupled with other studies of innervation of prostatic stroma (Brushing H, Schmidt, R. A, Tanagho, E. A, [1978] Invest. Urol. 15(4): 288-290; Watanabe, H., Shima, M., Kojima, M., Ohe, H. L. [1989] Pharmacol. Res. 21 (Suppl. 2): 85-94) suggest that cholinergic innervation influences epithelial behavior, while adrenergic innervation influences stromal tonus (excitability). These observations have provided a rationale for the use of, for example, alpha blockers in the treatment of BPH. The effects of alpha blockers (Downie, J. W. and Bialik, G. J. [1988] J. Pharmacal. Exp. Ther. 246(1): 352-358) can also account for improvements in symptoms of BPH as a result of dampening of dysfunctional striated sphincter behavior by the alpha blockers.

Studies have also shown that there are several tachykinins (for example, substance P [SP], calcitonin gene related peptide [CGRP], neurokinin A, bradykinin, and nerve growth factor [NGF]) that can influence the tonus of smooth muscle (Hakanson, et al., [1987] Neuroscience 21(3): 943-950). Neurotransmitter receptors have been quantified throughout the prostate (e.g., NPY, VIP, SP, leu-enkephalin (L-enk), met-enkephalin, 5-HT, somatostatin, acetylcholinesterase positive fibers (ACTH), and dopamine beta-hydroxylase (DBH) (Crowe, R., Chapple, C. R., Burnstock, G. The Human Prostate Gland: A Histochemical and Immunohistochemical Study of Neuropeptides, Serotonins, Dopamine beta-Hydroxylase and Acetylcholinesterase in Autonomic Nerves and Ganglia). There is some variation in receptor density at different prostatic sites in benign prostatic hyperplasia.

Changes in electrophysiologically recorded cellular behavior and in concentration of neuropeptides within the spinal cord have been shown to be a secondary consequence of mechanical pinch to the tail muscles of a rat, catheter stimulation of the posterior urethra, and electrostimulation of a peripheral nerve. Dyssynergia between the detrusor and the urethral sphincter is a significant finding in prostatodynia patients. Denervation of the prostate has been shown to produce dramatic changes within the prostatic epithelium. Thus there is evidence that experimentally induced alterations in neurological influences can be produced in the sacral, spinal cord, bladder or urethra through mechano-, electro-, chemical or thermal (microwave, laser) methods to change irritative behavior. However, there have been no known attempts to use neurotoxins for therapeutic applications.

There is poor correlation between the degree of prostatic enlargement and the severity of symptoms. While 80% of men age 70 show BPH on transrectal ultrasound scans, only 20% seek surgery (Coffey, D. S. and Walsh, P. C. [1990] Urol. Clin. North Am. 17(3): 461-475), the treatment of choice for BPH (Fowler, F. J. Jr., Wennberg. J. E., Timothy, R. P. [1988] J. Amer. Med. Assoc. 259(20): 3022-3028). Symptoms of irritation may far exceed symptoms expected based on the size of the prostate. Symptoms may improve after surgical treatment of BPH by procedures such as transurethral resection of the prostate (TURF) (Christensen, Aagaard, M. M. J., Madsen, P.O. [1990] Urol. Clin. North Am. 17(3): 621-629), balloon dilation (Dowd, J. B. and Smith, J. J. III [1990] Urol. Clin. North Am. 17(3): 671-677), or prostatic hyperthermia (Baert, L., Ameye, F., Willemen, P., et al. [1990] J. Urol. 144: 1383-1386). However, symptoms persist in as many as 15% of all BPH patients (Baert, L., Ameye. F., Willemen, P., et al. [1990] J. Urol. 144: 1383-1386; Wennberg, J. E., Mully, A. G., Hanley, D., Timothy, R. P., Fowler, F. J., Roos, R. P., Barry, M. J. et al. [1988] J. Amer. Med. Assoc. 259: 3027-3030). Up to 25% of BPH patients have secondary procedures in long term follow-up studies, suggesting that surgical approaches do not address the fundamental mechanisms that produce BPH, i.e., the faulty neurological influence (control mechanism) on the integrity of the lower urinary tract.

The need for repeated surgeries, the morbidity and mortality associated with TURP and the cost of surgery have led to the development of some non-surgical approaches such as androgen ablation (McConnell. J. D., [1990] Urol. Clin. North Am. 11(3): 661-670) and the use of alpha blockers discussed above, but few medical or surgical treatments to date have produced a restoration of void behavior to normal state (flow rate of about 25 cc/sec and void volume of about 400 cc).

OBJECTS AND SUMMARY OF THE PRESENT INVENTION

The present invention uses chemical and non-chemical methods, particularly neurotoxins, to modulate neuronally-mediated urologic and related disorders, such as neurogenic bladder dysfunction. Such methods can be also be used to treat BPH and related conditions such as prostatitis. The instant invention also may remove triggers of changes in the CNS; by non-chemical methods including biofeedback, or by chemical methods that treat BPH and other urological conditions by the administration of substances that block various neurological activities, such as, for example, selected neurotoxins including botulinum toxin.

It is an object of the instant invention to provide safe, inexpensive, out-patient methods for the prevention and treatment of urological-neurological dysfunctional states or conditions, for example, prostatic enlargement.

It is a further object of the present invention to provide compositions for this therapeutic goal. It is a still further object of the present invention to provide dosages and methods of administration for compositions useful for the prevention and treatment of neurological-urological conditions.

In accordance with one aspect of the present invention, there are provided methods of treating urological-neurological conditions, including neurogenic bladder dysfunction, in mammals, said methods comprising the step of administering a therapeutically effective amount of at least one neurotoxin to such a mammal. It is preferred that the neurotoxin inhibits synaptic function. Such inhibition produces selective denervation, and, for example, atrophy of the prostate and reversal of irritative symptoms associated with prostatic enlargement. In one embodiment of the instant invention, the neurotoxin induces dysfunction of the presynaptic neuronal terminal by specific binding and blockade of acetylcholine release at myoneural junctions and at cholinergic junctions generally. Such a neurotoxin can be, for example, botulinum toxin type A (BOTOX®, Allergan).

In accordance with another aspect of the present invention, a method is provided for treating a specific urological-neurological condition. Preferably, the urological-neurological condition is neurogenic bladder dysfunction. In one aspect, the neurogenic bladder dysfunction is not characterized by the symptom of urinary retention. This method comprises the step of administering a therapeutic amount of a botulinum toxin into the urinary sphincter of a patient with neurogenic bladder dysfunction, thereby relieving a symptom of said neurogenic bladder dysfunction. In a preferred embodiment, a symptom of neurogenic bladder dysfunction includes recurrent bladder infection, incontinence, and urge incontinence. The neurogenic bladder dysfunction can include a spastic sphincter.

In another embodiment of the present invention, the method for treating a neurogenic bladder dysfunction comprises the step of administering a therapeutic amount of a botulinum toxin into the bladder wall of a patient with neurogenic bladder dysfunction, thereby relieving a symptom of said neurogenic bladder dysfunction. In a preferred embodiment, a symptom of neurogenic bladder dysfunction includes urinary retention, recurrent bladder infection, incontinence, and urge incontinence. The neurogenic bladder dysfunction can include a spastic bladder. The neurogenic bladder dysfunction may be secondary to a disease condition selected from the group consisting of Parkinson's disease, a spinal cord injury, a stroke, multiple sclerosis, and a spasm reflex. Preferably, treatment according to methods of the present invention result in increased bladder capacity.

Preferably, the neurotoxin is safe, highly selective and easy to deliver, including when combined with other therapies. Other useful neurotoxins include capsaicin, resinoferatoxin and a-bungotoxin. Delivery of the neurotoxin can be by any suitable means. A convenient and localized method of delivery is by injection.

A therapeutically effective amount of the neurotoxin is the dosage sufficient to inhibit neuronal activity for at least one week, more preferably one month, most preferably for approximately 6 to 8 months or longer. Dosing can be single dosage or cumulative (serial dosing), and can be readily determined by one skilled in the art. Neurotoxin can be delivered serially (i.e., one time per month, one time per every six months) so that the therapeutic effect can be optimized. Such a dosage schedule is readily determined by one skilled in the art based on, e.g., patient size and the condition to be treated, and will depend on many factors, including the neurotoxin selected, the condition to be treated, the degree of irritation, and other variables. One suggested course of treatment for BPH is 200 units of BOTOX® every 3-4 months, as indicated by therapeutic requirements. Other suggested dosages of botulinum toxins are discussed in detail below.

The aforementioned methods of treatment should be particularly useful for the long-term control of neurological-urological disorders, such as the symptoms of neurogenic bladder dysfunction and the symptoms of prostatic enlargement, without the need for surgical intervention. Furthermore, the methods of the instant invention provide for control of neurological-urological disorders, e.g., BPH and related conditions, in a highly selective manner, without the potential side effects and treatment failures associated with current treatment modalities.

Other objects of the present invention will be readily apparent to those of ordinary skill in the art.

DETAILED DESCRIPTION OF THE PREFERRED EMBODIMENT

"Urological-neurological condition or disorder" includes many medical conditions in urology rooted in a spastic dysfunction and/or degeneration of the sacral reflex arcs. Examples of such conditions include pelvic pain (e.g., interstitial cystitis, endometriosis, prostatodynia, urethral instability syndromes), pelvic myofascial elements (e.g., levator sphincter, dysmenorrhea, anal fistula, hemorrhoid), urinary incontinence (e.g., motor or sensory, unstable bladder, unstable sphincter), prostate disorders (e.g., BPH, prostate cancer), recurrent infection (secondary to sphincter spasticity), and urinary retention (secondary to spastic sphincter, hypertrophied bladder neck), and neurogenic bladder dysfunction (e.g., Parkinson's Disease, spinal cord injury, stroke, multiple sclerosis, spasm reflex) and other such urological conditions of a nervous etiology.

The prostatic enlargement that can be treated according to the methods of the instant invention can be of any etiology. The instant invention is particularly suited for the treatment of prostatic hyperplasia, especially benign prostatic hyperplasia. The present invention can also be used for the treatment of enlargement of the prostate with inflammation (prostatitis), particularly abacterial prostatitis. In addition, the methods of the instant invention can be used for the treatment of prostatodynia.

In accordance with another aspect of the present invention, a method is provided for treating a urological-neurological condition. Preferably, the urological-neurological condition is neurogenic bladder dysfunction. In one embodiment, preferred neurogenic bladder dysfunctions to treat include dysfunctions where only the bladder (detrusor muscle) is spastic, i.e., there is no sphincter involvement; and/or dysfunctions where only the sphincter is spastic, i.e., there is no bladder (detrusor muscle) involvement. In another embodiment, preferred neurogenic bladder dysfunctions to treat include dysfunctions where there is a combined dysfunction, i.e., both the bladder and the urinary sphincter(s) spasm or contract simultaneously.

In one aspect of this embodiment, the method comprises the step of administering a therapeutic amount of a botulinum toxin into the urinary sphincter of a patient with neurogenic bladder dysfunction, thereby relieving a symptom of said neurogenic bladder dysfunction. Another preferred symptom of a neurogenic bladder dysfunction to relieve is increased incidents of UTIs (urinary tract infections) or recurrent infection. Another preferred symptom to relieve includes urge incontinence and incontinence. Methods of the present invention may relieve (i.e. treat, reduce, eliminate, or minimize) the symptoms of neurogenic bladder dysfunction. Preferably, a neurogenic bladder dysfunction to treat to treat by the method of administering into a urinary sphincter is primarily characterized by urinary incontinence. In one embodiment, a preferred neurogenic bladder dysfunction to treat by the method of administering into a urinary sphincter does not include neurogenic bladder dysfunctions characterized by urinary retention.

Methods of the present invention are useful for easing the difficulty some neurogenic bladder dysfunction patients have in relaxing the urinary sphincter muscle. Difficulty in relaxing the urinary sphincter muscle causes difficulty in emptying the bladder, which can lead to urinary retention and recurrent urinary tract infections. Causes of urinary sphincter spasm include interruptions in the nerve pathways to the bladder occurring above the sacrum. This nerve damage results in a loss of sensation and/or motor control and is often seen in stroke, Parkinson's disease, spina bifida, diabetes, pelvic surgery, or invertebral disc herniation, and most forms of spinal cord injuries. Causes for the neurogenic dysfunction may be unknown, thus neurogenic dysfunction which may be treated by the present invention may also include idiopathic cases, including those due to anxiety or aging.

In another aspect of this embodiment of the present invention, the method for treating a neurogenic bladder dysfunction comprises the step of administering a therapeutic amount of a botulinum toxin into the bladder wall of a patient with a neurogenic bladder dysfunction, thereby relieving a symptom of the neurogenic bladder dysfunction. A neurogenic bladder dysfunction which is treatable by methods of the invention includes bladder spasticity. Preferred symptoms to relieve using the instant methods include urge-type incontinence, recurrent bladder infection, incontinence, and urinary retention. Causes of neurogenic spastic bladder and urge-type dysfunction include interruptions in the nerve pathways to the bladder occurring above the sacrum. This nerve damage can result in a loss of sensation and/or motor control and is often seen in stroke, Parkinson's disease, spina bifida, diabetes, pelvic surgery, or invertebral disc herniation, and most forms of spinal cord injuries. Causes for the neurogenic dysfunction may be unknown, thus neurogenic dysfunction which may be treated by the present invention may also include idiopathic cases, including those due to anxiety or aging. In a preferred embodiment, bladder capacity is increased by treatment according to the methods of the present invention.

The methods of the present invention preferably comprise the administration of a botulinum toxin. The botulinum toxin useful for methods of the present invention include botulinum toxin type A, botulinum toxin type B, botulinum toxin type C, botulinum toxin type D, botulinum toxin type E, botulinum toxin type F, and botulinum toxin type G. Preferred botulinum toxins to use includes botulinum toxin type A and botulinum toxin type B. Preferably, botulinum toxin type A is used, and even more preferably, BOTOX®, is used. Other forms of botulinum toxin that are compatible with the present invention include chimeric or hybrid botulinum toxins, see, e.g., U.S. Pat. No. 5,939,070, which is incorporated by reference herein in its entirety; recombinantly made botulinum toxins, see, e.g., U.S. Pat. No. 5,919,665, which is incorporated by reference herein in its entirety; and retargeted botulinum toxins, see, e.g., U.S. Pat. Nos. 5,989,545 and/or 6,461,617, which are incorporated by reference herein in their entirety. Retargeted botulinum toxins refer to botulinum toxins that are attached to a non-native targeting moiety with affinity for the selected target tissue. Formulations of botulinum toxin that are compatible with the present invention include depot formulations, e.g., polymeric implants, microspheres, wafers, and gels, for sustained or controlled release. See, e.g., U.S. Pat. Nos. 6,585,993; 6,506,399; 6,306,423; 6,312,708; 6,383,509, all of which are incorporated herein by reference in their entirety.

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex) is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven generally immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake appears to take place through lower affinity receptors, as well as by the process of phagocytosis and or pinocytoscis in many types of cells.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of a vesicle-merging with the membrane docking, thereby preventing of the cell so that the contents of the vesicle will be ejected from the cell. This process is called exocytosis of vesicle content.

Botulinum toxins have been used in clinical settings for the treatment of neuromuscular disorders characterized by hyperactive skeletal muscles (i.e. motor disorders). In 1989 a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem, J* 1;339 (pt 1):159-65:1999, and *Mov Disord,* 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrena-* line Release From Cultured Mouse Brain, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1987. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373-1412 at 1393; Bigalke H., et al., *Botulinum A Neurotoxin Inhibits Non-Cholinergic Synaptic Transmission in Mouse Spinal Cord Neurons in Culture*, Brain Research 360;318-324:1985; Habermann E., *Inhibition by Tetanus and Botulinum A Toxin Of the release of [$^3$H]Noradrenaline and [$^3$H]GABA From Rat Brain Homogenate*, Experientia 44;224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $>3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56;80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1\text{-}2 \times 10^8$ $LD_{50}$ U/mg or greater; purified botulinum toxin type B with an approximately 156 kD molecular weight with a specific potency of $1\text{-}2 \times 10^8$ $LD_{50}$ U/mg or greater, and; purified botulinum toxin type F with an approximately 155 kD molecular weight with a specific potency of $1\text{-}2 \times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. Neurology, 48:249-53:1997.

It has been reported that botulinum toxin type A has been used in clinical settings as follows: (1) about 75-125 units of BOTOX® per intramuscular injection (multiple muscles) to treat cervical dystonia; (2) 5-10 units of BOTOX® per intramuscular injection to treat glabellar lines (brow furrows) e.g., 5 units injected intramuscularly into the procerus muscle and 10 units injected intramuscularly into each corrugator supercilii muscle); (3) about 30-80 units of BOTOX® to treat constipation by intrasphincter injection of the puborectalis muscle; (4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid; (5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired); (6) to treat upper limb spasticity following stroke by intramuscular injections of BOTOX® into five different upper limb flexor muscles, as follows: (a) flexor digitorum profindus: 7.5 U to 30 U; (b) flexor digitorum sublimus: 7.5 U to 30 U; (c) flexor carpi ulnaris: 10 U to 40 U; (d) flexor carpi radialis: 15 U to 60 U; (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session; (7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection. Any of the aforementioned dosages, along with dosages disclosed elsewhere in this application, are appropriate for use in the present invention.

Additionally, intramuscular botulinum toxin has been used in the treatment of tremor in patient's with Parkinson's disease, although it has been reported that results have not been impressive. Maijama-Jyons, J., et al., Tremor-Predominant Parkinson's Disease, Drugs & Aging 16(4);273-278:2000.

It is known that botulinum toxin type A can have an efficacy for up to 12 months (European J. Neurology 6 (Supp 4): S111-S1150:1999), and in some circumstances for as long as 27 months, when used to treat glands, such as in the treatment of hyperhydrosis. See e.g. Bushara K., Botulinum toxin and rhinorrhea, Otolaryngol Head Neck Surg 1996; 114(3):507, and The Laryngoscope 109:1344-1346:1999. However, the usual duration of an intramuscular injection of BOTOX® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A Botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, Nauny-Schmiedeberg's Arch. Pharmacol. 1976; 292, 161-165, and Habermann, Nauny-Schmiedeberg's Arch. Pharmacol. 1974; 281, 47-56 showed that botulinum toxin is able to ascend to the spinal area by retrograde transport. As such, a botulinum toxin injected at a peripheral location, for example intramuscularly, may be retrograde transported to the spinal cord.

A botulinum toxin has also been proposed for the treatment of rhinorrhea, (chronic discharge from the nasal mucous membranes, i.e. runny nose), rhinitis (inflammation of the nasal mucous membranes), hyperhydrosis and other disorders mediated by the autonomic nervous system (U.S. Pat. No. 5,766,605), tension headache, (U.S. Pat. No. 6,458,365), migraine headache (U.S. Pat. No. 5,714,468), post-operative pain and visceral pain (U.S. Pat. No. 6,464,986), pain treatment by intraspinal toxin administration (U.S. Pat. No. 6,113, 915), Parkinson's disease and other diseases with a motor disorder component, by intracranial toxin administration (U.S. Pat. No. 6,306,403), hair growth and hair retention (U.S. Pat. No. 6,299,893), psoriasis and dermatitis (U.S. Pat. No. 5,670,484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a botulinum toxin into the upper and lower esophageal, pyloric and anal sphincters)), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977) and neurogenic inflammation (U.S. Pat. No. 6,063,768). Additionally, controlled release toxin implants are known (see e.g. U.S. Pat. Nos. 6,306,423 and 6,312,708).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of Clostridium (Clostridium tetani and Clostridium botulinum, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for ganglioside receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Without being bound by theory, the basis for the treatment of the neurological-urological conditions according to the instant invention is the removal or modulation of the neural basis for the dysfunctional regulation of the affected tissue. For example, the modulation of the neural basis of prostate glandular dysfunction can be accomplished by any non-surgical means known in the art. Such means can include, for example, biofeedback, α-blockers, pharmacological methods, and the use of one or more neurotoxins to inhibit synaptic function in the affected gland. It is preferred that the neurotoxin cause long-lasting inhibition of synaptic function, preferably greater than one week, more preferably greater than one month, most preferably six to eight months or longer. Such neurotoxins can include, for example, capsaicin, resinoferatoxin, a-bungotoxin, terodotoxin and botulinum toxin. Botulinum toxin is a preferred neurotoxin according to the instant invention, particularly botulinum toxin A, more particularly BOTOX® (Allergen).

The toxin can be formulated in any pharmaceutically acceptable formulation in any pharmaceutically acceptable form. Such forms and formulations include liquids, powders, creams, emulsions, pills, troches, suppositories, suspensions, solutions, and the like. The toxin can also be used in any pharmaceutically acceptable form supplied by any manufacturer.

In a preferred embodiment in accordance with the method of the instant invention, the neurotoxin is botulinum toxin type A. Therapeutically effective amounts of botulinum toxin can be any amounts or doses that are less than a toxic dose, for example, less than about 3000 IU/70 kg male or about 43 IU per kg, preferably between 100 IU/70 kg male or about 1.4 IU per kg, up to about 1200 IU/70 kg or about 17 IU per kg. Preferred amounts of botulinum toxin to administer includes amounts between about 20 IU per 70 kg male or about 0.3 IU per kg, amounts of about 30 IU per 70 kg male or about 0.4 IU per kg, about 40 IU per 70 kg male or about 0.6 IU per kg, to about 100 IU per 70 kg male or about 1.4 IU per kg. The dosages can be given as a single dose, or as divided doses, for example, divided over the course of four weeks.

In another embodiment, if the neurotoxin is botulinum toxin type B, the dosage is approximately 50 times greater than the functionally equivalent dosage of botulinum toxin type A. For example, dosages of botulinum toxin type B can include dosages of at least about 20 I.U. per dose to about 1000 I.U. per dose, and so in, increments of 10 I.U. (i.e., 30 I.U., 40 I.U., . . . 100 IU, 110 IU.), and so on, up to 10,000 I.U. or greater.

The neurotoxins of the instant invention can be administered by any suitable means. In the preferred embodiment of the invention, botulinum toxin is administered by injection. Such injection can be administered to any affected area. For example, in one embodiment, the neurotoxin can be injected urethroscopically into the prostate with 200 IU with single or serial dosing. For example, one suggested course of treatment for BPH and other conditions that can be treated using the method of the invention is 200 units of BOTOX® every 3-4 months, as indicated by therapeutic requirements. Preferably the neurotoxin is injected every three days until a therapeutic effect is achieved or up to about 2500 units.

The following techniques are used in this invention:

Tissue Preparation for Light Microscopy

Tissues are fixed in 6% paraformaldehyde in 0.1 M phosphate buffer, pH 7.2, for 24 hours, dehydrated in graded alcohol and xylene, and embedded in paraffin. Sections are cut and stained with appropriate stains, such as hematoxylin/eosin.

Tissue Preparation for Election Microscopv

Tissues are collected and fixed in 2.5% glutaraldehyde in 0.1 M phosphate buffer, pH 7.2, for 1 hour at 4° C., then incubated with 0.1% osmium tetroxide for 1 hour and embedded in EPON. Ultrathin sections (80 nm) are prepared and stained with lead citrate/uranyl acetate and examined vrith an electron microscope (philips, model 201).

Tunel Stain for Apoptosis

The tissue is fixed and embedded as described above. The tissues are deparaffinized and reacted with Proteinase K (Boehringer). They are further treated with peroxidase and TDT enzyme and placed in a humidifier set at 30° C. for one hour. The sections are washed and anti-digoxigenin-peroxidase is added for 30 minutes, followed by staining with nickel-DAB (diaminobenzene).

Immunohistochemistry Studies

The presence of the neuropeptides VIP, SP, NYP, L-Enk and calcitonin gene-related peptide (CGRP) as well as the expression of transforming growth factor beta (TGF-beta), transforming growth factor alpha (TGF-alpha), epidermal growth factor (EGF) and basic fibroblast growth factor (bFGF) are determined in prostatic tissues using appropriate monoclonal antibodies. Use of neurotoxins results in prostatic atrophy, which should be reflected by lower levels of growth factors in treated prostatic tissue.

Sections are incubated overnight at room temperature with primary antibodies followed by immunostaining with avidin-biotin-peroxidase (Vectastain Elite ABC, Vector Labs, USA). Rabbit polyclonal antiserum against the neurotransmitters VIP, CGRP, SP,NPY and L-Enk (Peninsula Labs, USA) is used in these preparations, at dilutions of 1:8000 to 1:12,000. Immunocytochemical controls consist of preabsorbing the primary antiserum with appropriate antigen, or their substitution with normal serum (Blasi, J., Chapman, E. R., Yamas, S., Binz, T., Niemann, H and Jahn, R. [1993] The EMBO Journal 12: 4821-4828; Black, J. D. and Dolly, J. O. [1986] J. Cell Biol. 103; 535-544; Linial, M. [1995] Is. J. Med. Sci. 31: 591-595). After mounting on slides, sections are counter-stained with eosin, dehydrated and coverslipped.

Western Blot Analysis of Growth Factor Expression

Treated and untreated prostate cell homogenates are examined for expression of growth factors by Western blot analysis. Cell homogenate protein is separated by electrophoresis on SDS-PAGE (7%), then transferred electrophoretically overnight to nitrocellulose paper (Towbin, H., et al., [1979] Proc. Nat. Acad. Sci. 76(9): 4350-4379). The nitrocellulose paper is soaked for one hour at room temperature in 0.5% non-fat dry milk dissolved in phosphate buffered saline, and further soaked overnight at 4° C. in blocking solution (2% bovine serum albumin in 10 mM Tris/0.15 M NaCl/0.1% sodium azide, pH 7.4). The nitrocellulose membranes are incubated with antibodies (IgG fractions of anti-TGF-beta, anti-TGF-alpha, anti-EGF and anti-bFGF) purified by protein A ($1\times10^6$ cpm/ml) in blocking buffer for 1 hour. The membrane is washed with PBS containing Nonidet P-40 between incubations. X-O-mat AR2 film (Kodak) is exposed to the membrane at −70° C. and films are developed to examine the expression of growth factors.

Determination of c-fos and c-myc Expression

Expression of c-fos and c-myc in treated and untreated prostatic tissue is determined by Northern blot analysis as follows. Tissue is homogenized in lysis buffer for 15 seconds or until the tissue homogenizes. Sodium acetate is added and the solution is mixed by swirling. An equal volume of water-saturated phenol is added and mixed by inversion, followed by addition of chloroform/isoamyl alcohol. The solution is vortexed vigorously for 30 seconds, and allowed to settle on ice for 15 minutes. The solution is centrifuged for 10-20 minutes at 4° C. After centrifugation, the aqueous phase is carefully aspirated and placed in a new polypropylene tube. One volume of isopropanol is added and the solution is mixed by swirling. The solution is placed in a −20° C. freezer for at least 60 minutes to precipitate RNA. After precipitation, the tube is centrifuged for 10 minutes, and the supernatant is decanted, leaving the RNA pellet. One ml of ethanol is added, and the tube is centrifuged for additional 10 minutes. The aqueous phase is discarded, and the pellet is washed with 100% ethanol by vortexing. The RNA pellet is redissolved in 0.4 ml of lysis buffer. The RNA is re-precipitated by the addition of 100% ethanol and incubation at −20° C. freezer for at least 60 minutes. The solution is centrifuged and the supernatant discarded. RNA concentration is determined by diluting 5 μL of sample into 995 μL of DEPC water and measuring the ratio of absorbance at 260/280 nm.

The following examples are provided by way of describing specific embodiments without intending to limit the scope of the invention in any way.

EXAMPLE 1

This Example describes denervation of the prostate.

Unilateral denervation of the prostate is carried out by removal of the pelvic ganglia, which overlie the prostate of the rat. This approach preserves the functional integrity of the bladder and posterior urethra and removes the possibility for artifact arising from major disturbances in blood flow or micturation. Control animals undergo sham operations without concurrent denervation of the prostate. After denervation, the animals are allowed to recover and maintained prior to collection of the prostate. The prostate is preserved, prepared for light microscopy and examined histologically. The major findings are (1) reduced epithelial cell height primarily due to a decrease in the clear supranuclear zone (due to a reduction in the amount and size of the apical cistemae and the endoplasmic reticulum); (2) major changes in protein expression on SDS gel electrophoresis (the endoplasmic reticulum is important in protein synthesis) (3) modest reduction in the number of secretory granules; (4) an increase in intracellular vacuoles, intercellular empty spaces and reduction in microvilli on the cell surface; and (5) a significant increase in nerve growth factor (NGF) content ipsilateral to the denervation relative to the control group (188±10 vs. 46±20 vs. 29±16 pg/g wet tissue (±SD) NGF is known to influence only sympathetic and sensory neurons. N=15 in both the control and experimental groups.

EXAMPLE 2

This Example describes the effect of neurotoxin injection on normal prostate: rat prostate.

Rats were randomly assigned into three groups. The first group received a single acute dose of Botulinum toxin type A (BOTOX® Allergen) of 5, 10 or 15 IU. These animals were sacrificed one week after injection. The second group received a series of 4 weekly injections of 5 IU of Botulinum toxin and were sacrificed at 5 weeks. Control rats received saline injections. Injections were performed as single or serial injections into the left and/or right ventral lobe of the prostate. Note that an injection of methylene blue into one lobe of the rat prostate showed immediate diffusion into the opposite lobe. Thus, there was communication between the prostate lobes and therefore the contralateral lobe could not be used as a true comparative control.

The weight of each prostate ventral lobe collected from healthy animals was approximately 0.50 gram. All toxin-treated animals showed shrinkage of prostate volume, first in the injected lobe, and with subsequent injections, reduction in the overall volume. After four serial injections, the left prostate lobe weighed 0.12-0.17 gram, while the right prostate lobe weighed 9.10-0.14 grams. This represented a reduction of over two-thirds of the original size.

EXAMPLE 3

This Example describes the effect of neurotoxin injection on urological dysfunctions: human data.

Three patients with recalcitrant voiding dysfunction were treated with injections of botulinum toxin (BOTOX®) as follows. Patient 1 was a 47-year-old male who was incontinent secondary to an injury sustained at the cervical vertebrae (level C6-C7) sustained 14 months previously. Urodynamics on presentation revealed a bladder capacity of 30 cc and a weak sphincter (peak urethral pressure of 40 cm water). He had failed multiple pharmacological regimes and was intolerant to penile clamp/condom devices.

He received four weekly 200 IU botulinum toxin injections into the bladder neck for total dose of 800 IU. Post-injection, his bladder capacities ranged from 300-400 cc with oxybutinin and 150-200 cc without Oxybutinin. Peak bladder pressures pre-injection had been 200-cm water, compared to post injection bladder pressures of 40 cm of water. The patient was continent with a penile clamp after treatment with botulinum toxin. In addition, walking and erections improved due to reduced bladder spasticity.

Patient 2 was a 55 year old T12 paraparetic female secondary to traumatic injury 14 years previous. The patient presented with urge incontinence, and had been on self-catheterization every 2 hours during the day and two times at night. The patient received injections into the lateral bladder wall in two weekly injections of 200 IU each for a total of 400 IU of botulinum toxin. The patient's voiding diary data revealed pre-injection capacities of between 150-200 cc. Post injection, diary data indicated bladder capacity increased to 300-400 cc. In addition, the patient no longer had annoying constant urge type dysfunction, slept through the night and was continent on self-catheterization every 4 hours.

Patient 3 was a 65 year old male with disabling perineal pain following radiation treatment for prostatic cancer. The patient had failed medical therapy. He was treated with one 200 IU injection of botulinum toxin into the external urethral sphincter. The patient experienced dramatic relief of testicle pain and had far less severe pain in the shaft of the penis. Erections were not affected.

EXAMPLE 4

This Example describes the determination of the smallest effective dose.

Rats are injected in the prostate ventral lobes with single and serial doses of botulinum toxin (BOTOX®). The prostates are harvested at different time intervals to determine the smallest effective dose, as well as the morphological and physiological changes taking place with time. The smallest effective dose is defined as that dose that would demonstrate a decrease in prostate volume.

To assess the response to electrical field stimulation, preparations are mounted between two platinum electrodes placed in the organ bath. The tension of the preparations is adjusted. Transmural stimulation of nerves is performed using a Danted Neuromatic 2000 Simulator delivering single-wave pulses at supramaximal voltage with a duration of 0.8 milliseconds at a frequency of 0.5 to 80 hertz. The polarity of the electrodes is changed after each pulse by means of a polarity-changing unit. The train duration is five seconds and the train interval 120 seconds. Isometric tension is recorded by using a Gould thermo-array 8-channel recorder. Separate experiments are performed to determine the preload teflsion producing optimal responses. In addition, the effect of the electric field stimulation in the presence of different concentrations of individual neuropeptides is determined. These neuropeptides are 10-20 μM adrenaline, 10 μM clonidine, 5-50 mM regitine, 10 nM-0.1 μM acetylcholine, 1-3 μM atropine, 1 nM-10 μM nifedipine, 1-10 nM VIP and 1-250 nM NPY. The effect of nitroprusside (a nitric oxide releasing substance) and methylene blue (a guanylate cyclase inhibitor) on prostate tone and contraction resulting from field stimulation also is examined in these tissues.

EXAMPLE 5

This Example describes the effect of botulinum toxin on rat prostatic tissue: comparison of hormonally intact rats to hormonally deprived rats.

To determine if there is any interaction between the neurotoxin and testicularly-derived hormones, studies are performed which will examine the interaction of the neurotoxin with hormonal components. These studies will compare prostatic tissue treated with botulinum toxin harvested from rats that have undergone orchiectomy (hormonally depleted rats) and prostatic tissue from rats treated with botulinum toxin that did not undergo orchiectomy. Fifty-two age-matched rats are treated as described below. Four healthy rats will undergo a sham operation consisting of anesthesia induction, exposure of the prostate and injection of 0.2 cc saline into the left ventral lobe of the prostate. Three rats are given bilateral orchiectomy with no injection to the prostate (hormonally depleted controls), five rats will have orchiectomy and injection of 0.2 ml saline in the left ventral lobe (hormonal depletion+surgical stress control). Four groups of rats receive botulinum injections of 0.5 IU, 1.0 IU, 1.5 IU and 2.5 IU only (hormonally intact experimental rats). Sixteen rats undergo bilateral orchiectomy. Eight of these rats are treated with a single injection of 2.5 IU botulinum toxin into the left ventral lobe 5 weeks after surgery. All rats are sacrificed after six weeks, and the harvested prostate is prepared for examination as described above. A similar atrophic effect on glandular epithelium is expected.

EXAMPLE 6

This Example describes the effects of botulinum toxin on patients.

Patients affected by benign prostatic hyperplasia, abacterial prostatis, or prostatodynia are studied both before and after treatment with botulinum toxin. Patients are eligible for inclusion in this study if they are affected by BPH between the ages of 40 and 80, or if they are between 25 and 60 and have been diagnosed with abacterial prostatitis or prostatodynia. Preferred patients are those who are not good surgical candidates. Patients are evaluated prior to treatment by determination of prostate specific antigen levels (PSA), evaluation of urodynamic parameters (cystometrogram, urethral pressure profile and flowmetry), determination of American Urological Association (AUA) symptom score (Barry, M. J., et al., [1992] J. Urol, 148: 1549-1557), maintenance of a voiding diary, and examination of the prostate by transrectal ultrasound with biopsy (for BPH patients only). One week after initial evaluation is completed, the patient is injected urethroscopically with 200 IU of botulinum toxin as either single unilateral injections, serial unilateral injections or 1.5 bilateral injections. BPH patients are treated by TURP or undergo control TURP-biopsy 7 days after single injection or 5 weeks after serial injections. The harvested prostatic tissues are prepared for examination as described in the previous Examples. The patients are re-evaluated after injection using the same parameters examined during the initial evaluation.

EXAMPLE 7

This example describes treatment of patients with hyperreflexive bladder due to neurogenic bladder dysfunction.

Several patients with hyperreflexive bladders with symptoms including bladder infection, incontinence, and urge incontinence due to neurogenic bladder dysfunction as a result of spinal cord injury will be treated by injection of an effective amount of BOTOX®, for example, preferably about 20-30 IU or up to 100-200 IU into the detrusor muscle of the bladder. The BOTOX® is divided up into multiple doses, such as, for example, 10 doses, and injected into multiple sites on the bladder, sparing the trigone. Patients will be under light sedation. A significant increase in the mean maximum bladder capacity and significant decrease in the mean maximum detrusor voiding pressure is expected post-injection. It is predicted that maximal efficacy of botulinum injection is achieved within seven days post injection. It is expected that most patients will report that both sleep quantity and quality improved, and also will report a decrease or absence of incontinence and a significant decrease in voiding symptoms. Additional dosing with BOTOX® may be performed if required for maximal response. Clinical responses are predicted to last from four to more than one year (e.g., fourteen months) with no adverse effects with the treatment being observed.

EXAMPLE 8

This Example describes treatment of patients with difficulty relaxing the urinary sphincter muscle.

A patient with multiple sclerosis is diagnosed with neurogenic bladder dysfunction after presenting with urge-type dysfunction, and/or difficulty in emptying the bladder. The patient may also suffer from repeated urinary tract infections due to retained urine in the bladder. The patient is treated with an effective amount of BOTOX®, for example, preferably about 20-30 IU or up to 100-200 IU of BOTOX® into the external sphincter. Treatment will consist of multiple transurethral injections (such as, for example, four injections of 2.5 milliliters each) spaced equally around the sphincter at the level of the striated sphincter. Injections will be directed deeper than collagen injections to target nerve terminals innervating skeletal muscle. It is expected that within a matter of days, the patient's bladder functioning will be normal or near-normal and the patient will report a disappearance and/or reduction of symptoms. Additional dosing with BOTOX® may be performed if required for maximal response. It is expected that the patient will report that symptoms do not begin to reappear until six months or more have passed. It is then expected that treatment described above can be repeated successfully.

The foregoing description of the invention is exemplary for purposes of illustration and explanation. It will be apparent to those skilled in the art that changes and modifications are possible without departing from the spirit and scope of the invention. All documents cited herein are hereby incorporated by reference. It is intended that the following claims be interpreted to embrace all such changes and modifications.

What is claimed is:

1. A method for treating a patient with a neurogenic bladder dysfunction, said method comprising the step of injecting a therapeutically effective amount of botulinum toxin type A into the lateral bladder wall of a patient with said neurogenic bladder dysfunction, thereby treating a symptom of said neurogenic bladder dysfunction.

2. The method of claim 1, wherein said neurogenic bladder dysfunction is secondary to a disease condition selected from the group consisting of Parkinson's disease, a spinal cord injury, a stroke, multiple sclerosis, and a spasm reflex.

3. The method of claim 1, wherein the step of injection comprises a single injection.

4. The method of claim 1, wherein the step of injection comprises injecting a gel comprising the botulinum toxin.

5. The method of claim 1, wherein the step of injecting results in increased bladder capacity.

6. The method of claim 1, wherein the therapeutically effective amount of botulinum toxin type A is up to 2500 units.

7. The method of claim 1, wherein the therapeutically effective amount of botulinum toxin type A is about 1.4 IU/kg to 17.1 IU/kg of botulinum toxin type A.

8. The method of claim 1, wherein the therapeutically effective amount of botulinum toxin type A is 200 IU of botulinum toxin type A.

* * * * *